US010722205B2

United States Patent
Liang et al.

(10) Patent No.: US 10,722,205 B2
(45) Date of Patent: Jul. 28, 2020

(54) METHOD AND APPARATUS FOR OPTIMIZING BLOCKING GRATING FOR CONE BEAM CT IMAGE SCATTERING CORRECTION

(71) Applicant: Shenzhen Institutes of Advanced Technology, Shenzhen, Guangdong (CN)

(72) Inventors: Xiaokun Liang, Guangdong (CN);
Yaoqin Xie, Guangdong (CN);
Zhicheng Zhang, Guangdong (CN);
Tianye Niu, Guangdong (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 228 days.

(21) Appl. No.: 15/850,561

(22) Filed: Dec. 21, 2017

(65) Prior Publication Data
US 2018/0132807 A1    May 17, 2018

Related U.S. Application Data

(63) Continuation of application No. PCT/CN2016/104864, filed on Nov. 7, 2016.

(51) Int. Cl.
*A61B 6/00* (2006.01)
*A61B 6/03* (2006.01)
(Continued)

(52) U.S. Cl.
CPC ............ *A61B 6/5282* (2013.01); *A61B 6/032* (2013.01); *A61B 6/035* (2013.01); *A61B 6/06* (2013.01);
(Continued)

(58) Field of Classification Search
CPC .. A61B 6/032; A61B 6/06; A61B 6/40; A61B 6/4085; A61B 6/42; A61B 6/4208;
(Continued)

(56) References Cited

U.S. PATENT DOCUMENTS 6,618,466 B1 *  9/2003  Ning ................... A61B 6/032
                                                    378/62
6,876,718 B2 *  4/2005  Tang ................... A61B 6/032
                                                    378/4
(Continued)

FOREIGN PATENT DOCUMENTS

CN    101987021    3/2011
CN    103961129    8/2014
(Continued)

OTHER PUBLICATIONS

Liang et al., "Scatter correction of linear accelerator cone-beam CT image", Chin J. Med Imaging Technol, vol. 32, No. 4, Apr. 30, 2016, pp. 619-622 (English language abstract enclosed).
(Continued)

*Primary Examiner* — Allen C. Ho
(74) *Attorney, Agent, or Firm* — Bayramoglu Law Offices LLC

(57) ABSTRACT

A method and apparatus for optimizing a blocking grating for cone beam CT image scattering correction, wherein the method comprises: scanning a blocking grating to establish a swinging model thereof; setting initial coordinates of the blocking grating along a longitudinal direction of a detector in an initial projection, and establishing an objective function between CBCT image data missing voxel values and the coordinates of the blocking grating along the longitudinal direction of the detector according to the swinging model; minimizing the objective function with a mesh-adaptive direct search algorithm to generate optimized coordinates of the blocking grating along the longitudinal direction of the
(Continued)

detector. The present disclosure proposes a brand new scattering correction method not requiring any source compensation, performs a mathematical optimization modeling of the data missing caused by the blocking grating in the image domain, quantitatively evaluates the influence on the reconstructed image by a blocker, solves a geometric optimal structure of the blocker using a mesh-adaptive direct search algorithm, and lays a solid theory foundation for the scattering correction method based on the blocker measurement.

12 Claims, 5 Drawing Sheets

(51) Int. Cl.
G01T 1/161 (2006.01)
A61N 5/10 (2006.01)
A61B 6/06 (2006.01)

(52) U.S. Cl.
CPC .............. *A61B 6/40* (2013.01); *A61B 6/42* (2013.01); *A61B 6/4208* (2013.01); *A61B 6/4233* (2013.01); *A61B 6/4291* (2013.01); *A61B 6/44* (2013.01); *A61B 6/4429* (2013.01); *A61B 6/4435* (2013.01); *A61B 6/4441* (2013.01); *A61B 6/4447* (2013.01); *A61B 6/482* (2013.01); *A61B 6/483* (2013.01); *A61B 6/52* (2013.01); *A61B 6/5205* (2013.01); *A61B 6/5211* (2013.01); *A61B 6/5258* (2013.01); *A61B 6/54* (2013.01); *A61B 6/545* (2013.01); *A61B 6/58* (2013.01); *A61B 6/582* (2013.01); *A61B 6/583* (2013.01); *A61N 5/1049* (2013.01); *G01T 1/161* (2013.01); *A61B 6/4085* (2013.01); *A61B 6/542* (2013.01); *A61N 2005/1061* (2013.01)

(58) Field of Classification Search
CPC ... A61B 6/4233; A61B 6/4241; A61B 6/4291; A61B 6/482; A61B 6/483; A61B 6/52; A61B 6/5205; A61B 6/5211; A61B 6/5258; A61B 6/5282; A61B 6/035; A61B 6/44; A61B 6/4429; A61B 6/4435; A61B 6/4441; A61B 6/4447; A61B 6/54; A61B 6/542; A61B 6/545; A61B 6/58; A61B 6/582; A61B 6/583
USPC ..... 378/4, 6, 7, 16, 19, 98.8, 154, 210, 901, 378/147, 149, 205, 207; 250/370.09
See application file for complete search history.

(56) References Cited

U.S. PATENT DOCUMENTS

| | | | | |
|---|---|---|---|---|
| 7,308,072 B2* | 12/2007 | Rührnschopf | ......... | A61B 6/032 378/7 |
| 7,366,279 B2* | 4/2008 | Edic | ....... | A61B 6/032 378/150 |
| 7,443,945 B2* | 10/2008 | Bruder | .......... | A61B 6/032 378/7 |
| 7,471,759 B2* | 12/2008 | Rinkel | ........ | A61B 6/5282 378/18 |
| 7,486,773 B2* | 2/2009 | Maltz | .......... | A61B 6/4233 250/358.1 |
| 7,496,171 B2* | 2/2009 | Rinkel | ....... | G01T 1/29 378/207 |
| 7,535,987 B2* | 5/2009 | Matsuda | ........... | G01N 23/046 378/159 |
| 7,751,525 B2* | 7/2010 | Rührnschopf | ........ | G06T 11/005 378/7 |
| 7,778,384 B2* | 8/2010 | Proksa | .......... | A61B 6/032 378/7 |
| 7,801,266 B2* | 9/2010 | Nöttling | ............... | G06T 11/005 378/18 |
| 7,835,485 B2* | 11/2010 | Bruder | ......... | A61B 6/032 378/7 |
| 7,957,502 B2* | 6/2011 | Manabe | ............... | G06T 11/005 378/6 |
| 8,000,435 B2* | 8/2011 | Bertram | ............... | G06T 11/005 378/6 |
| 8,009,794 B2* | 8/2011 | Partain | .......... | A61B 6/032 378/150 |
| 8,045,676 B2* | 10/2011 | Hayashida | .......... | G01N 23/046 378/4 |
| 8,077,826 B2* | 12/2011 | Ruimi | ............ | A61B 6/032 378/19 |
| 8,144,829 B2* | 3/2012 | Zhu | ............ | A61B 6/032 378/7 |
| 8,199,873 B2* | 6/2012 | Star-Lack | ........... | A61B 6/5282 378/7 |
| 8,199,879 B2* | 6/2012 | Star-Lack | ............. | A61B 6/032 378/7 |
| 8,290,116 B2* | 10/2012 | Wiegert | .............. | G06T 11/005 378/147 |
| 8,326,011 B2* | 12/2012 | Star-Lack | ............ | G06T 7/0012 378/7 |
| 8,391,577 B2* | 3/2013 | Takahashi | ........... | A61B 6/5282 378/154 |
| 8,483,471 B2* | 7/2013 | Wu | ........ | A61B 6/032 378/70 |
| 8,644,577 B2* | 2/2014 | Kappler | ................. | A61B 6/032 378/7 |
| 8,705,827 B2* | 4/2014 | Zhu | ......... | G06T 5/002 378/7 |
| 8,818,065 B2* | 8/2014 | Yang | ..................... | G06T 11/005 382/131 |
| 8,873,703 B2* | 10/2014 | Ruimi | ................... | A61B 6/032 378/7 |
| 8,989,469 B2* | 3/2015 | Fahimian | ............... | A61B 6/032 378/19 |
| 9,047,696 B2* | 6/2015 | Petersilka | ............. | G06T 11/006 382/128 |
| 9,263,164 B2* | 2/2016 | Goldammer | ......... | A61B 6/4035 |
| 9,320,477 B2* | 4/2016 | Liu | ........ | A61B 6/032 |
| 9,330,458 B2* | 5/2016 | Star-Lack | ............. | G06T 11/005 |
| 9,367,903 B2* | 6/2016 | Goldammer | ......... | A61B 6/4035 |
| 9,980,682 B2* | 5/2018 | Ahn | ............... | A61B 6/03 |
| 10,271,811 B2* | 4/2019 | Lu | ......... | A61B 6/5282 |
| 10,342,504 B2* | 7/2019 | Star-Lack | ............ | G06T 7/0012 |
| 10,588,592 B2* | 3/2020 | Scott | ............ | G01T 1/2985 |
| 2005/0072929 A1 | 4/2005 | Chuang et al. | | |

FOREIGN PATENT DOCUMENTS

| | | |
|---|---|---|
| CN | 104161536 | 11/2014 |
| CN | 104540451 | 4/2015 |
| CN | 106408543 | 2/2017 |

OTHER PUBLICATIONS

Niu et al., "Scatter correction for full-fan volumetric CT using a stationary beam blocker in a single full scan", Medical Physics, vol. 38, No. 11, Nov. 30, 2011, pp. 6027-6038.

* cited by examiner nsMETHOD AND APPARATUS FOR OPTIMIZING BLOCKING GRATING FOR CONE BEAM CT IMAGE SCATTERING CORRECTION

TECHNICAL FIELD

The present disclosure relates to the field of medical imaging related to cone beam CT applications, and particularly, to a method and apparatus for optimizing a blocking grating for cone beam CT image scattering correction.

BACKGROUND

This section intends to provide a background or context for the embodiments of the present disclosure described in the claims. Although being included in this section, the descriptions herein will not be deemed as the prior art.

The technology of Image Guide Radiation Therapy (IGRT) is the most important means in the precise radiotherapy at present. The IGRT can provide exact position information for precise lesion localization and tumor irradiation, and has been widely used in the modern minimally invasive surgery and radiotherapy. The X-ray CBCT installed beside the treatment couch is an important means for implementing image guide nowadays.

However, in accompany with the expansion of irradiation volume in a single projection, the quality of the cone-beam computed tomography (CBCT) image will be rapidly deteriorated due to the restriction of a fundamental physical process—scattering pollution. The traditional CT reconstruction theory assumes that the X-ray is in a rectilinear propagation, and the detected ray intensity attenuates with the integral index. The scattered photons deviate from the incident beam direction and cannot be modelled into the traditional CT reconstruction theory, which is the error source of the CT image reconstruction. Studies show that the strength of the scattering signal monotonically increase while the irradiation volume of the X-ray expands. The CBCT scattering pollution seriously affects the precision of the CT value, the detectability of the target with a low contrast, and the accuracy of the dose calculation, and those disadvantages directly disable the CBCT for wide clinical applications. When a human body is scanned in a CBCT system having no scattering correction, the CT value error caused by the scattering artifact can reach 350 HU, thus the CBCT is mainly used for the primary localization and positioning, and its further applications in the intervention and radiotherapy are seriously restricted. Therefore the scattering correction is the problem to be firstly solved for improving the quality of the CBCT image.

The currently known scattering correction methods mainly include two types, i.e., the pre-processing method and the post-processing method. The pre-processing method performs a scattering correction mainly by attaching a hardware device to prevent the scattered photons from arriving at the detector, so that the scattering signal and associated statistic noises are suppressed in the projection. Two typical examples of the pre-processing method include expanding the air gap between the detector and the object, and using the anti-scatter grid. With the expansion of the air gap, the detectivity of the diffused scattered photons is decreased, while the source signal will not be influenced. But the method is restricted by the physical space of the CBCT device itself, while requiring adding the X-ray dose to compensate for the increase of the distance, thus it is not practical in clinical practices. The anti-scatter grid uses lead meshes focusing at the ray source and can block the scattered light from the non-focusing incident angle. The method has the defect that the attenuation efficiency of the scattered light is not high. Currently, the commercial grid only provides an SPR reduction rate of about 3 times, and cannot ensure the quality of the CBCT image under the high scattering environment. In addition, it also requires adding the patient's exposure dose to compensate for the intensity of the source ray attenuated.

In view of the limitation of the pre-processing method, the post-processing method is more studied at present. The post-processing means perform a scattering correction after obtaining the projection image of the scattering pollution in the traditional way. Since it is impossible to theoretically predict the random scattering time, the scattering noises still remain in the image even a perfect pre-processing method is used. There are many pre-processing methods, including analytical modeling method, Monte Carlo simulation method, source modulation method and measurement method. The analytical modeling method deems that the scattering signal is a response after the source signal passes through a scattering kernel which is generally obtained through a measurement or simulation. If the scattering kernel has the characteristic of unchanged linear translation space, the calculation speed will be fast. But correspondingly, the scattering estimation accuracy is limited and the parameters shall be tediously adjusted for a complex object. The Monte Carlo simulation method establishes a more accurate statistical model for the scattering signal by simulating the interaction between the photons and the illuminated object. But the method has a huge calculation amount, thus much time is cost, and the current computer computing power restricts its application in the CBCT image reconstruction that almost requires a real time processing. The source modulation method adds a high-frequency modulator between the X-ray source and the object, and separate the scattering signal and the source signal from each other in the frequency domain according to different response characteristics thereof. The method does not increase the patient exposure dose or scanning time, but the clinical application effect is restricted by actual physical factors, such as the spiral arm vibration and big focus size.

A measurement-based scattering correction is an implementation method most similar to the present disclosure. The method adds a beam blocking grating in front of the CBCT ray source to estimate the scattering signal, so that a shadow area only containing the scattering signal is formed on the detector. Since the scattering distribution mainly concerns the low-frequency components and slightly disturbed by the blocking grating, the whole scattering distribution can be obtained by a scattering sampling interpolation for the shadow area of the detector. The measurement-based method can obtain an accurate scattering estimation, but the cost is the loss of the source signal. Thus, people usually need to scan each angle twice (one using the blocking grating, and the other removing the blocking grating), or move the blocking grating in the scanning process.

The measurement-based scattering correction method is possible since the blocker has a low cost and can be easily made. The Chinese patent No. 201410380731.3 proposes a method and apparatus for cone beam CT scattering correction based on complementary grating. The invention performs a scattering correction of a projection image through complementary grating scanning and a small calculation amount, and the scattering correction slice images can be reconstructed using the scattering-corrected projection image. The Chinese patent No. 201010574162.8 proposes a CT system and a scattering correction method for the same. The invention acquires the bright field image, places the blocker between the detector and the object to be scanned, and obtains the attenuation projection image after scanning; next, scans the object to be scanned and the scattering corrector, respectively, to obtain a projection image set and a scattering correction image; next, generates a scattering signal distribution according to the bright field image, the scattering correction image and the attenuation projection image, and finally obtains a corrected projection according to a difference between the projection image set and the scattering signal distribution.

Most of the existed scattering correction methods using the blocker need to scan twice to compensate for the blocked original projection signal, and they cannot be put into the clinical application since the patient's expose dose is increased. In addition, those methods are used in the desktop CBCT experimental platform; since such experimental platform replaces the rotation of the light source and the detector with the rotation of the object to be scanned, the isocenter of the CT system is stable, and the projection positions of the blocker at different timing are almost consistent with each other, thus the difficulty for performing a scattering correction using the blocker is largely decreased, and those methods are only applicable for the lab desktop CBCT system with a stable isocenter. However, in the clinical CBCT system, due to the vibration in the rack rotation process and the deviation of the rotation isocenter, the projection position of the blocking grating varies with the rotation of the rack, and it is difficult to accurately extract the scattering signal in the grating area.

SUMMARY OF THE DISCLOSURE

An objective of the present disclosure is to provide a method and apparatus for optimizing a blocking grating for cone beam CT image scattering correction, so as to solve the existing problem that the number of scans is increased and it is difficult to accurately extract a scattering signal when the scattering correction is performed using a blocker.

In order to achieve the above objective, the embodiments of the present disclosure provide a method for optimizing a blocking grating for cone beam CT image scattering correction, comprising: scanning a blocking grating to establish a swinging model thereof; setting initial coordinates of the blocking grating along a longitudinal direction of a detector in an initial projection, and establishing an objective function between CBCT image data missing voxel values and the coordinates of the blocking grating along the longitudinal direction of the detector according to the swinging model; minimizing the objective function with a mesh-adaptive direct search algorithm to generate optimized coordinates of the blocking grating along the longitudinal direction of the detector.

In order to achieve the above objective, the embodiments of the present disclosure further provide an apparatus for optimizing a blocking grating for cone beam CT image scattering correction, comprising a memory, a processor and a computer program stored in the memory and executable in the processor, wherein the processor performs the following operations when executing the computer program: scanning a blocking grating to establish a swinging model thereof; setting initial coordinates of the blocking grating along a longitudinal direction of a detector in an initial projection, and establishing an objective function between CBCT image data missing voxel values and the coordinates of the blocking grating along the longitudinal direction of the detector according to the swinging model; minimizing the objective function with a mesh-adaptive direct search algorithm to generate optimized coordinates of the blocking grating along the longitudinal direction of the detector.

In order to achieve the above objective, the embodiments of the present disclosure further provide a computer readable storage medium, wherein the computer readable storage medium stores a computer program which causes the processor to perform the following operations when being executed: scanning a blocking grating to establish a swinging model thereof; setting initial coordinates of the blocking grating along a longitudinal direction of a detector in an initial projection, and establishing an objective function between CBCT image data missing voxel values and the coordinates of the blocking grating along the longitudinal direction of the detector; minimizing the objective function with a mesh-adaptive direct search algorithm to generate optimized coordinates of the blocking grating along the longitudinal direction of the detector.

The method and apparatus for optimizing a blocking grating for cone beam CT image scattering correction in the embodiments of the present disclosure propose a brand new scattering correction method not requiring any source compensation and adaptive to the clinical CBCT. The present disclosure establishes the mathematical model for swinging of the projection of the blocking grating caused by the isocenter deviation of the cantilever and the vibration of the rack by means of the image segmentation method, thereby successfully applying the blocking grating into clinical cone beam CT scattering corrections; performs a mathematical optimization modeling of the data missing caused by the blocking grating in the image domain, quantitatively evaluates the influence on the reconstructed image by the blocker, solves the geometric optimal structure of the blocker using a mesh-adaptive direct search algorithm, lays a solid theory foundation for the scattering correction method based on the blocker measurement, and further reveals the importance of the blocker design to the clinical cone beam CT scattering correction.

BRIEF DESCRIPTION OF THE DRAWINGS

In order to more clearly describe the technical solutions in the embodiments of the present disclosure, the drawings to be used in the descriptions of the embodiments will be briefly introduced as follows. Obviously, the drawings in the following descriptions just illustrate some embodiments of the present disclosure, and a person skilled in the art can obtain other drawings from them without paying any creative effort. In which.

DETAILED DESCRIPTION OF THE EMBODIMENTS

Next, the technical solutions in the embodiments of the present disclosure will be clearly and completely described with reference to the drawings in the embodiments of the present disclosure. Obviously, those described are just a part rather than all of the embodiments of the present disclosure. Based on the embodiments of the present disclosure, any other embodiment obtained by a person skilled in the art without paying any creative effort shall fall within the protection scope of the present disclosure.

As known to a person skilled in the art, the embodiment of the present disclosure may be implemented as a system, an apparatus, a device, a method or a computer program product. Thus the present disclosure can be specifically implemented as complete hardware, complete software (including firmware, resident software, microcode, etc.), or a combination of hardware and software.

Next, the principle and spirit of the present disclosure are elaborated in details as follows with reference to several representative embodiments of the present disclosure.

The embodiments of the present disclosure propose a mathematical model of an 'interdigital' blocking grating for the quality of a reconstructed image. The mathematical model considers the grating dithering, and introduces a mesh-adaptive direct search algorithm for solving the objective function, so as to obtain a geometric design of a blocking grating suitable for the clinical CBCT scattering correction. Next, the designed blocking grating is placed in front of the ray source, the scattering distribution of each projection is estimated in an interpolation method after the scattering sample is accurately extracted, and finally a scattering corrected image is precisely reconstructed in a semi-fan scanning reconstruction algorithm, thus the clinical CBCT scattering correction is achieved by a single scan.

Figure 1:
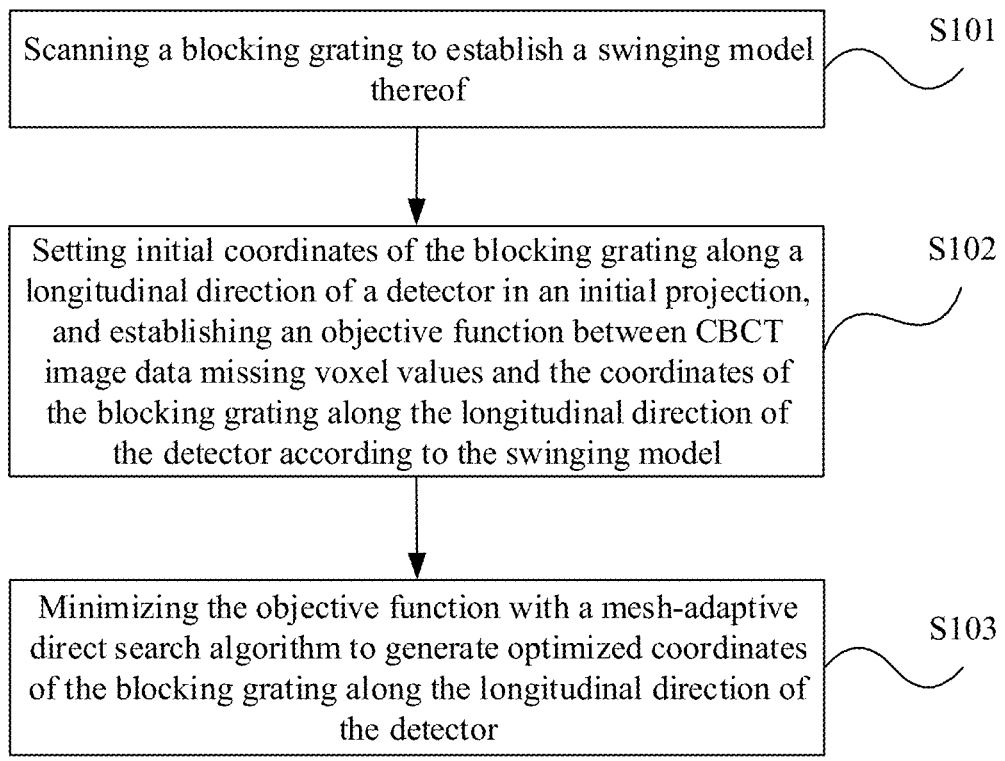
FIG. 1 illustrates a processing flowchart of a method for optimizing a blocking grating for cone beam CT image scattering correction in an embodiment of the present disclosure.

FIG. 1 illustrates a processing flowchart of a method for optimizing a blocking grating for cone beam CT image scattering correction in an embodiment of the present disclosure. As illustrated in FIG. 1, the method comprising:

step S101: scanning a blocking grating to establish a swinging model thereof;

step S102: setting initial coordinates of the blocking grating along a longitudinal direction of a detector in an initial projection, and establishing an objective function between CBCT image data missing voxel values and the coordinates of the blocking grating along the longitudinal direction of the detector according to the swinging model;

step S103: minimizing the objective function with a mesh-adaptive direct search algorithm to generate optimized coordinates of the blocking grating along the longitudinal direction of the detector.

Figure 2:
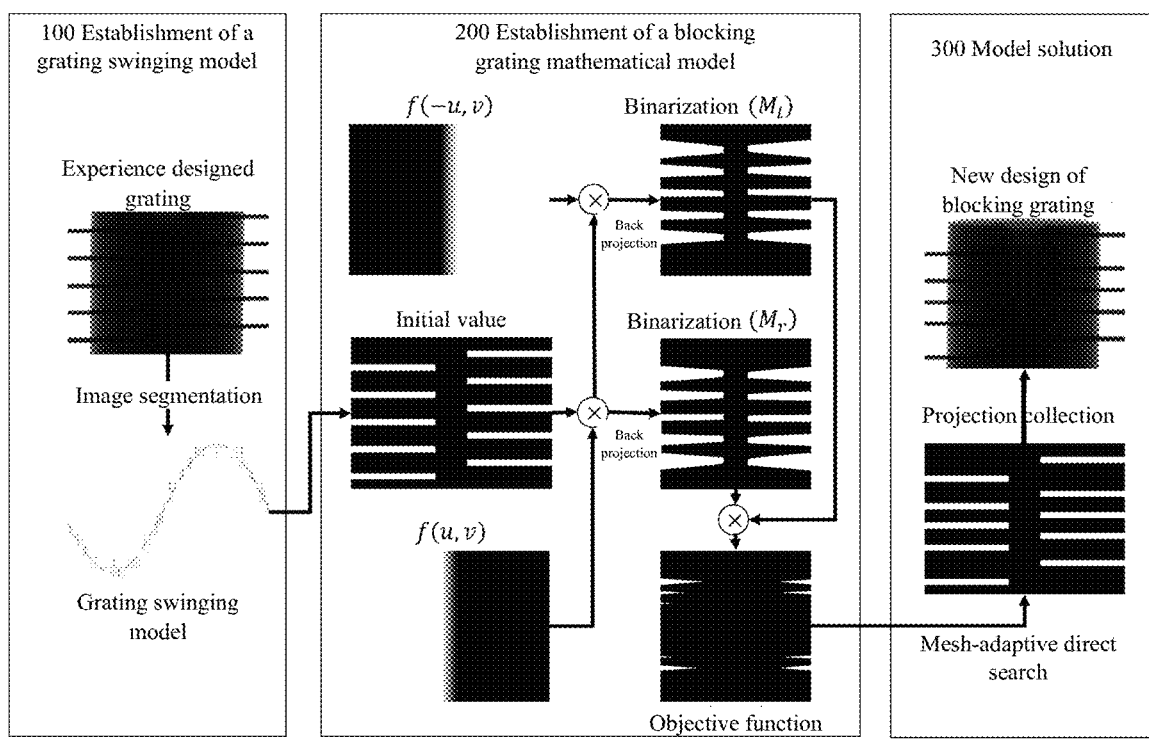
FIG. 2 illustrates a principle diagram of a method for optimizing a blocking grating for cone beam CT image scattering correction in an embodiment of the present disclosure.

FIG. 2 illustrates a principle diagram of a method for optimizing a blocking grating for cone beam CT image scattering correction in an embodiment of the present disclosure. Step S101 in FIG. 1 is corresponding to 100 in FIG. 2 (establishment of a grating swinging model), Step S102 in FIG. 1 is corresponding to 200 in FIG. 2 (establishment of a blocking grating mathematical model), and step S103 in FIG. 1 is corresponding to 300 in FIG. 2 (model solution). In the embodiment as illustrated in FIG. 2, ten gratings are used in an example to explain the principle.

In step S101 of this embodiment, with reference to 100 of FIG. 2, a blocking grating firstly shall be designed based on experiences, and then scanned for studying the swinging model of a lead bar projection caused by the isocenter deviation of the cantilever and vibration of the rack in the clinical CBCT. In a preferred embodiment, the designed blocking grating is an 'interdigital' grating.

On the projection of the blocking grating obtained by scanning, an appropriate threshold value of the blocking grating is determined using the maximum between-class variance method (OTSU), an image segmentation is performed based on the threshold value to convert the interested area into a binary image, so as to obtain coordinate values of the central point of the blocking grating in the direction, and acquire the relation between the angle of the rack and the position change of the blocking grating. Namely, the coordinate position of the blocking grating is determined through the generated binary image, and the swinging model of the blocking grating can be obtained according to the coordinate position of the blocking grating.

In step S102 of this embodiment, with reference to 200 of FIG. 2, the objective function of the blocking grating and the number of missing voxels of the image data will be established. The principle is that as the interval between the blocking gratings increases, the number of missing voxels of the image data reconstructed with two groups of semi-fan scanning algorithms decreases. While ensuring the accuracy of scattering estimation, the design of the blocking grating shall ensure the minimization of the number of missing voxels of the image data. Thus, it is possible to design an objective function about the placement position of the blocking grating.

Firstly, the initial coordinates of the blocking grating along the longitudinal direction of the detector in the initial projection shall be set. The number of the blocking gratings may be set as n, then the coordinates of the $i^{th}$ blocking grating along the longitudinal direction of the detector in the initial projection are:

$$G=(g_1, g_2, \ldots, g_n)^T \qquad (1)$$

Next, the projection image of the blocking grating in each projection is simulated according to the swinging model and the initial coordinates. In the embodiment, the projection image of the blocking grating is simulated, the blocked area is set as 1, and the unblocked area is set as 0. Due to the swinging and the isocenter deviation of the rack, the coordinate position of the blocking grating is different in each projection, wherein $d_j$ is the projection offset in the $j^{th}$ projection.

$$p_{i,j}(u,v) = \begin{cases} 1, & -\frac{U}{2} \leq u \leq -\frac{U}{2}+l, \ g_i+d_j \leq v \leq g_i+d_j+w_0 \\ 0, & \text{otherwise} \end{cases} \qquad (2)$$

$$i = 1, 3, 5, \ldots, n-1$$

$$p_{i,j}(u,v) = \begin{cases} 1, & \frac{U}{2}-l \leq u \leq \frac{U}{2}, \ g_i+d_j \leq v \leq g_i+d_j+w_0 \\ 0, & \text{otherwise} \end{cases} \qquad (3)$$

$$i = 2, 4, 6, \ldots, n$$

$p_{i,j}(u,v)$ in Equations (2) and (3) are images of singular blocking grating on left and right sides in the $j^{th}$ projection, U is a horizontal pixel width of the detector, $w_0$ is a width of the blocking grating, and u and v are horizontal and vertical coordinate values of the detector, respectively.

Equations (2) and (3) are added together to obtain:

$$P_j = \sum_{i=1}^{n} p_{i,j} \qquad (4)$$

$P_j$ is an image of the blocking grating in the $j^{th}$ projection.

M projections $P_j$ are multiplied by weighting functions f (u, v) and f (−u, v), respectively, for a back projection reconstruction to obtain:

$$M_l = BP\left(\sum_{j=1}^{m}(P_j \cdot f(u, v))\right) \qquad (5)$$

$$M_r = BP\left(\sum_{j=1}^{m}(P_j \cdot f(-u, v))\right) \qquad (6)$$

It can be found that among $M_l$ and $M_r$, the voxel value influenced by the blocking grating is non-zero, and the voxel value not influenced by the blocking grating is zero; $M_l \cdot M_r$ is a non-zero area, i.e., the missing voxels of the data after the reconstructed images of the left and right semi-fans are fused. The optimization design of the blocking grating requires that a binarized sum of the missing voxels of the data in the reconstruction volume shall be minimized. The establishment process of the objective function is illustrated in FIG. 2, and the following objective function can be obtained:

$$\bar{g} = \arg\min \|BNR(M_l) \cdot BNR(M_r)\|_1$$

s.t.

$$g_{i+1} - g_i > w_0 \; i=1,2,\ldots,n-1$$

$$g_{min} \leq \bar{g} \leq g_{max}$$

$$g_{i+1} - g_i > w_0 \; i=1,2,\ldots,n-1 \qquad (7)$$

wherein $g_{min} \leq \bar{g} \leq g_{max}$ is a constraint condition which means that the left and right gratings must be alternatively distributed, and the vertical coordinate of the gratings cannot exceed a range of the vertical coordinate of the detector.

In step S103 of the embodiment, with reference to 300 of FIG. 2, the initial parameters of the blocking grating are used as the initial values of the mesh-adaptive direct search algorithm to generate optimized coordinates of the blocking grating along the longitudinal direction of the detector, wherein the initial parameters of the blocking grating are uniformly distributed at an equal interval, and of course, other interval may be adopted.

Figure 3:
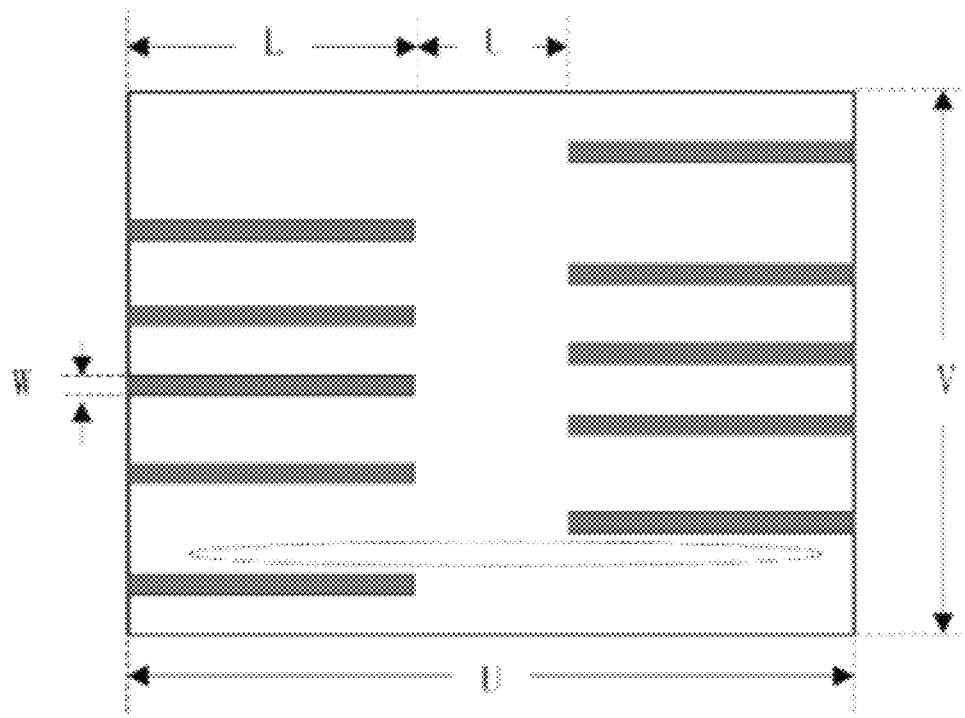
FIG. 3 illustrates a geometric model of an optimized blocking grating in an embodiment of the present disclosure.

The objective function is solved by introducing the mesh-adaptive direct search algorithm. In the optimization model mentioned herein, the vibration offset $d_j$ of the blocking grating caused by the isocenter deviations of the rack and the vibration is obtained by an object tracking. Currently, the optimization solutions include the mathematical programming method, the heuristic algorithm, the direct search method, etc. The optimization model of the blocking grating is strongly nonlinear, and provides no derivative information, thus the mathematical programming method cannot be employed. Although the heuristic algorithm, such as the simulated annealing algorithm or the genetic algorithm, has a better global search capability, its local search capability is not enough, and the convergence speed is very slow. Since one back projection operation shall be performed each time an objective function is generated, a lot of redundant iterations will occur and much time will be cost, if the objective function of the present disclosure employs the heuristic algorithm. The decision vectors of the mesh-adaptive direct search (MADS) algorithm may be discrete, continuous and binary; the objective function and its constraint condition may be the "black box function"; the MADS algorithm is adaptive to solve a multivariable mathematical model; thus the present disclosure employs the MADS algorithm to solve the optimization model of the blocking grating. During the solution, in a preferred embodiment, the parameters of the blocking gratings uniformly distributed are used as initial values of the MADS objective function, and the solved grating geometric model is illustrated in FIG. 3.

After the optimized blocking grating structure is obtained in the above steps, it is placed between the ray source and the object to be scanned. After the object projection is collected, the grating position is determined using the image segmentation based on the threshold value, and an interpolative estimation is performed for the scattering distribution using the collected scattering signal. The scattering corrected projection image is obtained by removing the scattering distribution from the original image. Next, the scattering corrected image is reconstructed using the semi-fan scan reconstruction algorithm based on the Parker function.

To be noted, although the operations of the method of the present disclosure are described in a particular sequence in the drawings, it does not requires or implies that those operations must be performed in that particular sequence, or the desired result must be achieved by performing all of the illustrated operations. Additionally or optionally, some steps may be omitted, multiple steps may be merged into one step, and/or one step may be divided into multiple steps.

After the method of the exemplary embodiment of the present disclosure is introduced, an apparatus for optimizing a blocking grating for cone beam CT image scattering correction in an exemplary embodiment of the present disclosure will be described as follows. Please refer to the implementation of the above method for the implementation of the apparatus, and the repeated content is omitted herein.

Figure 4:
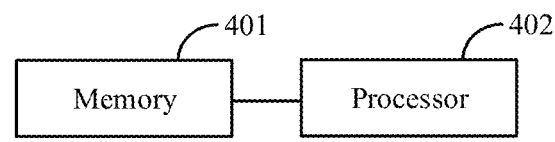
FIG. 4 illustrates a structure diagram of an apparatus for optimizing a blocking grating for cone beam CT image scattering correction in an embodiment of the present disclosure.

FIG. 4 illustrates a structure diagram of an apparatus for optimizing a blocking grating for cone beam CT image scattering correction in an embodiment of the present disclosure. As illustrated in FIG. 4, the apparatus comprises a memory 401, a processor 402 and a computer program stored in the memory 401 and executable in the processor 402, wherein the processor 402 performs the following operations when executing the computer program:

scanning a blocking grating to establish a swinging model thereof;

setting initial coordinates of the blocking grating along a longitudinal direction of a detector in an initial projection, and establishing an objective function between CBCT image data missing voxel values and the coordinates of the blocking grating along the longitudinal direction of the detector according to the swinging model;

minimizing the objective function with a mesh-adaptive direct search algorithm to generate optimized coordinates of the blocking grating along the longitudinal direction of the detector.

In the embodiment, the processor 402 further performs the following operations when executing the computer program:

on a projection of the blocking grating, determining an appropriate threshold value of the blocking grating using the maximum between-class variance method, performing an image segmentation based on the threshold value to generate a binary image, determining a coordinate position of the blocking grating through the generated binary image, and obtaining the swinging model of the blocking grating.

In the embodiment, the processor 402 further performs the following operations when executing the computer program:

setting the number of the blocking gratings as n, then coordinates of an $i^{th}$ blocking grating along the longitudinal direction of the detector in the initial projection are:

$$G=(g_1,g_2,\ldots,g_n)^T;$$

simulating an projection image of the blocking grating in each projection according to the swinging model and the initial coordinates;

performing a back projection reconstruction for each of the projection images;

establishing an objective function between missing voxel values of data after reconstructed images of left and right semi-fans are fused and the coordinates of the blocking grating along the longitudinal direction of the detector according to the images undergone the back projection reconstruction.

The embodiments of the present disclosure further provide a computer readable storage medium, wherein the computer readable storage medium stores a computer program which causes the processor to perform the following operations when being executed:

scanning a blocking grating to establish a swinging model thereof;

setting initial coordinates of the blocking grating along a longitudinal direction of a detector in an initial projection, and establishing an objective function between CBCT image data missing voxel values and the coordinates of the blocking grating along the longitudinal direction of the detector;

minimizing the objective function with a mesh-adaptive direct search algorithm to generate optimized coordinates of the blocking grating along the longitudinal direction of the detector.

In the embodiment, the computer program further causes the processor to perform the following operations when being executed:

on a projection of the blocking grating, determining an appropriate threshold value of the blocking grating using the maximum between-class variance method, performing an image segmentation based on the threshold value to generate a binary image, determining a coordinate position of the blocking grating through the generated binary image, and obtaining the swinging model of the blocking grating.

In the embodiment, the computer program further causes the processor to perform the following operations when being executed:

setting the number of the blocking gratings as n, then coordinates of an $i^{th}$ blocking grating along the longitudinal direction of the detector in the initial projection are:

$$G=(g_1,g_2,\ldots,g_n)^T;$$

simulating an projection image of the blocking grating in each projection according to the swinging model and the initial coordinates;

performing a back projection reconstruction for each of the projection images;

establishing an objective function between missing voxel values of data after reconstructed images of left and right semi-fans are fused and the coordinates of the blocking grating along the longitudinal direction of the detector according to the images undergone the back projection reconstruction.

Figure 5:
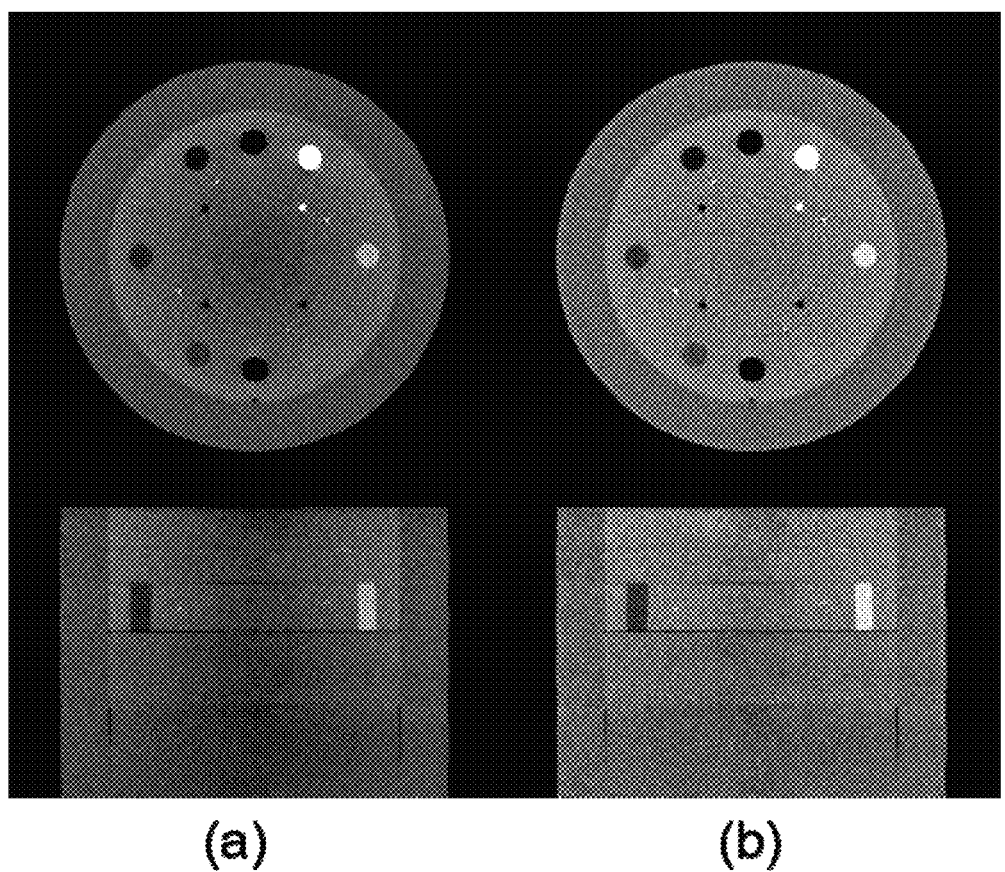
FIG. 5 illustrates a comparison diagram of actual correction effects obtained according to a method for optimizing a blocking grating in an embodiment of the present disclosure.

The blocking grating designed and optimized through the embodiments of the present disclosure has been tested, simulated and used to prove its feasibility. In the CBCT of Varian Trilogy, the Catphan504 die body is used for the test, and the scattering correction is performed using the blocking grating designed and optimized by the present disclosure. The CT error of the interested area drops from 115 HU to 11 HU, while the contrast is increased by 1.45 times. The correction effect is shown in FIG. 5, wherein column (a) is an image before the correction, and column (b) is an image after the correction.

The method and apparatus for optimizing a blocking grating for cone beam CT image scattering correction in the embodiments of the present disclosure propose a brand new scattering correction method not requiring any source compensation and adaptive to the clinical CBCT. The present disclosure establishes the mathematical model for swinging of the projection of the blocking grating caused by the isocenter deviation of the cantilever and the vibration of the rack by means of the image segmentation method, thereby successfully applying the blocking grating into clinical cone beam CT scattering corrections; performs a mathematical optimization modeling of the data missing caused by the blocking grating in the image domain, quantitatively evaluates the influence on the reconstructed image by the blocker, solves the geometric optimal structure of the blocker using a mesh-adaptive direct search algorithm, lays a solid theory foundation for the scattering correction method based on the blocker measurement, and further reveals the importance of the blocker design to the clinical cone beam CT scattering correction.

A person skilled in the art shall understand that the embodiment of the present disclosure can be provided as a method, a system or a computer program product. Therefore, the present disclosure can take the form of a full hardware embodiment, a full software embodiment, or an embodiment combining software and hardware aspects. Moreover, the present disclosure can take the form of a computer program product implemented on one or more computer usable storage mediums (including, but not limited to, a magnetic disc memory, CD-ROM, optical storage, etc.) containing therein computer usable program codes.

The present disclosure is described with reference to a flow diagram and/or block diagram of the method, device (system) and computer program product according to the embodiments of the present disclosure. It shall be understood that each flow and/or block in the flow diagram and/or block diagram and a combination of the flow and/or block in the flow diagram and/or block diagram can be realized by the computer program instructions. These computer program instructions can be provided to a general computer, a dedicated computer, an embedded processor or a processor of other programmable data processing device to generate a machine, such that the instructions performed by the computer or the processor of other programmable data processing devices generate the device for implementing the function designated in one flow or a plurality of flows in the flow diagram and/or a block or a plurality of blocks in the block diagram.

These computer program instructions can also be stored in a computer readable memory capable of directing the computer or other programmable data processing devices to operate in a specific manner, such that the instructions stored in the computer readable memory generate a manufactured article including an instruction device that implements the function(s) designated in one flow or a plurality of flows in the flow diagram and/or a block or a plurality of blocks in the block diagram.

These computer program instructions can also be loaded onto the computer or other programmable data processing devices, such that a series of operation steps is executed on the computer or other programmable devices to generate the processing realized by the computer, therefore the instructions executed on the computer or other programmable devices provide the steps for implementing the function designated in one flow or a plurality of flows in the flow chart and/or a block or a plurality of blocks in the block diagram.

Specific embodiments are used to elaborate the principle and the implementations of the present disclosure. The descriptions of those embodiments just intend to help the understanding of the method and the core idea of the present disclosure. Meanwhile, an ordinary person skilled in the art can change the implementations and the application range based on the idea of the present disclosure. In conclusion, the contents of the Specification shall not be understood as limitations to the present disclosure.

What is claimed is:

1. A method for optimizing a blocking grating for cone beam CT image scattering correction, comprising:
    scanning a blocking grating to establish a swinging model thereof;
    setting initial coordinates of the blocking grating along a longitudinal direction of a detector in an initial projection, and establishing an objective function between CBCT image data missing voxel values and the initial coordinates of the blocking grating along the longitudinal direction of the detector according to the swinging model;
    minimizing the objective function with a mesh-adaptive direct search algorithm to generate optimized coordinates of the blocking grating along the longitudinal direction of the detector.

2. The method for optimizing a blocking grating for cone beam CT image scattering correction according to claim 1, wherein scanning a blocking grating to establish a swinging model comprises:
    on a projection of the blocking grating, determining an appropriate threshold value of the blocking grating using a maximum between-class variance method, performing an image segmentation based on the appropriate threshold value to generate a binary image, determining a coordinate position of the blocking grating through the generated binary image, and obtaining the swinging model of the blocking grating.

3. The method for optimizing a blocking grating for cone beam CT image scattering correction according to claim 1, wherein setting initial coordinates of the blocking grating along a longitudinal direction of a detector in an initial projection comprises:
    setting a number of the blocking gratings as n, then coordinates of an $i^{th}$ blocking grating along the longitudinal direction of the detector in the initial projection are:

$G=(g_1,g_2,\ldots,g_n)^T$.

4. The method for optimizing a blocking grating for cone beam CT image scattering correction according to claim 1, wherein establishing an objective function between CBCT image data missing voxel values and the initial coordinates of the blocking grating along the longitudinal direction of the detector according to the swinging model comprises:
    simulating a projection image of the blocking grating in each projection according to the swinging model and the initial coordinates;
    performing a back projection reconstruction for the projection image of each projection;
    establishing an objective function between missing voxel values of data after reconstructed images of left semi-fan and right semi-fan are fused and the initial coordinates of the blocking grating along the longitudinal direction of the detector according to projection images undergone the back projection reconstruction.

5. The method for optimizing a blocking grating for cone beam CT image scattering correction according to claim 1, wherein minimizing the objective function with a mesh-adaptive direct search algorithm to generate optimized coordinates of the blocking grating along the longitudinal direction of the detector comprises:
    using initial parameters of the blocking grating as initial values of the mesh-adaptive direct search algorithm to generate the optimized coordinates of the blocking grating along the longitudinal direction of the detector.

6. The method for optimizing a blocking grating for cone beam CT image scattering correction according to claim 5, wherein the initial parameters of the blocking grating are uniformly distributed at an equal interval.

7. An apparatus for optimizing a blocking grating for cone beam CT image scattering correction, comprising a memory, a processor, and a computer program stored in the memory and executable in the processor, wherein the processor performs the following operations when executing the computer program:
    scanning a blocking grating to establish a swinging model thereof;
    setting initial coordinates of the blocking grating along a longitudinal direction of a detector in an initial projection, and establishing an objective function between CBCT image data missing voxel values and the initial coordinates of the blocking grating along the longitudinal direction of the detector according to the swinging model;
    minimizing the objective function with a mesh-adaptive direct search algorithm to generate optimized coordinates of the blocking grating along the longitudinal direction of the detector.

8. The apparatus for optimizing a blocking grating for cone beam CT image scattering correction according to claim 7, wherein the processor further performs the following operations when executing the computer program:
    on a projection of the blocking grating,
    determining an appropriate threshold value of the blocking grating using a maximum between-class variance method,
    performing an image segmentation based on the appropriate threshold value to generate a binary image,
    determining a coordinate position of the blocking grating through the generated binary image, and
    obtaining the swinging model of the blocking grating.

9. The apparatus for optimizing a blocking grating for cone beam CT image scattering correction according to claim 7, wherein the processor further performs the following operations when executing the computer program:
    setting a number of the blocking gratings as n, then coordinates of an $i^{th}$ blocking grating along the longitudinal direction of the detector in the initial projection are:

$G=(g_1, g_2, \ldots, g_n)^T$;

simulating a projection image of the blocking grating in each projection according to the swinging model and the initial coordinates;

performing a back projection reconstruction for the projection image of each projection;

establishing an objective function between missing voxel values of data after reconstructed images of left semi-fan and right semi-fan are fused and the initial coordinates of the blocking grating along the longitudinal direction of the detector according to projection images undergone the back projection reconstruction.

10. A non-transitory computer readable storage medium, wherein the non-transitory computer readable storage medium stores a computer program, which causes a processor to perform the following operations when being executed:

scanning a blocking grating to establish a swinging model thereof;

setting initial coordinates of the blocking grating along a longitudinal direction of a detector in an initial projection, and establishing an objective function between CBCT image data missing voxel values and the initial coordinates of the blocking grating along the longitudinal direction of the detector;

minimizing the objective function with a mesh-adaptive direct search algorithm to generate optimized coordinates of the blocking grating along the longitudinal direction of the detector.

11. The non-transitory computer readable storage medium according to claim 10, wherein the computer program causes the processor to perform the following operations when being executed:

on a projection of the blocking grating, determining an appropriate threshold value of the blocking grating using a maximum between-class variance method, performing an image segmentation based on the appropriate threshold value to generate a binary image, determining a coordinate position of the blocking grating through the generated binary image, and obtaining the swinging model of the blocking grating.

12. The non-transitory computer readable storage medium according to claim 10, wherein the computer program causes the processor to perform the following operations when being executed:

setting a number of the blocking gratings as n, then coordinates of an $i^{th}$ blocking grating along the longitudinal direction of the detector in the initial projection are:

$G=(g_1, g_2, \ldots, g_n)^T$;

simulating a projection image of the blocking grating in each projection according to the swinging model and the initial coordinates;

performing a back projection reconstruction for the projection image of each projection;

establishing an objective function between missing voxel values of data after reconstructed images of left semi-fan and right semi-fan are fused and the initial coordinates of the blocking grating along the longitudinal direction of the detector according to projection images undergone the back projection reconstruction.

* * * * *